US007041112B2

(12) United States Patent
Vargas et al.

(10) Patent No.: US 7,041,112 B2
(45) Date of Patent: May 9, 2006

(54) METHOD FOR TENSIONING AN INCISION DURING AN ANASTOMOSIS PROCEDURE

(75) Inventors: Jaime Vargas, Palo Alto, CA (US); Tenny Chang, Mountain View, CA (US); David Bombard, San Francisco, CA (US)

(73) Assignee: Cardica, Inc., Redwood City, CA (US)

( * ) Notice: Subject to any disclaimer, the term of this patent is extended or adjusted under 35 U.S.C. 154(b) by 52 days.

(21) Appl. No.: 10/842,998

(22) Filed: May 11, 2004

(65) Prior Publication Data

US 2004/0249415 A1 Dec. 9, 2004

Related U.S. Application Data

(63) Continuation of application No. 09/764,218, filed on Jan. 16, 2001, now abandoned.

(51) Int. Cl.
*A61B 17/08* (2006.01)
(52) U.S. Cl. .................... 606/153; 604/167.01
(58) Field of Classification Search ................ 606/151, 606/152, 153–155, 157, 198, 213, 219–220, 606/142; 600/215–217, 231–232, 235
See application file for complete search history.

(56) References Cited

U.S. PATENT DOCUMENTS

| 3,254,650 A | 6/1966 | Collito |
| 3,254,651 A | 6/1966 | Collito |
| 3,519,187 A | 7/1970 | Kapitanov et al. |
| 3,774,615 A | 11/1973 | Lim et al. |
| 4,214,587 A | 7/1980 | Sakura, Jr. |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,592 A | 6/1985 | Daniel |
| 4,553,542 A | 11/1985 | Schenck et al. |
| 4,593,693 A | 6/1986 | Schenck |
| 4,603,693 A | 8/1986 | Conta et al. |
| 4,607,637 A | 8/1986 | Berggren et al. |

(Continued)

FOREIGN PATENT DOCUMENTS

DE 19732234 A 1/1999

(Continued)

*Primary Examiner*—Julian W. Woo
*Assistant Examiner*—Victor Nguyen
(74) *Attorney, Agent, or Firm*—Anthony J. Josephson; Brian A. Schar

(57) ABSTRACT

A method for tensioning incisions made in a target vessel during an anastomosis procedure is provided. After an incision is made in a target vessel, incision tensioners are placed within the incision in order to tension the incision. The incision is tensioned when the incision tensioners are pulled taut in order to stretch the incision to a predetermined length or a predetermined force. The tensioners allow for proper grafting of a graft vessel to the target vessel in an end to side anastomosis. In addition, the incision tensioners allow the incision to have a known geometry, thereby allowing precise grafting of the graft vessel to the target vessel during the anastomosis procedure. After the incision is tensioned, the graft vessel is grafted to the target vessel using clips, sutures, staples or other anastomosis devices. One example of anastomosis clips are configured to capture the graft vessel and the target vessel such that the graft vessel grafts with the target vessel.

20 Claims, 4 Drawing Sheets

U.S. PATENT DOCUMENTS

| | | |
|---|---|---|
| 4,624,255 A | 11/1986 | Schenck et al. |
| 4,624,257 A | 11/1986 | Berggren et al. |
| 4,657,019 A | 4/1987 | Walsh |
| 4,665,906 A | 5/1987 | Jervis |
| 4,733,665 A | 3/1988 | Palmaz |
| 4,739,762 A | 4/1988 | Palmaz |
| 4,740,207 A | 4/1988 | Kreamer |
| 4,747,407 A | 5/1988 | Liu |
| 4,752,024 A | 6/1988 | Green et al. |
| 4,773,420 A | 9/1988 | Green |
| 4,776,337 A | 10/1988 | Palmaz |
| 4,787,899 A | 11/1988 | Lazarus |
| 4,795,458 A | 1/1989 | Regan |
| 4,872,874 A | 10/1989 | Taheri |
| 4,879,135 A | 11/1989 | Greco et al. |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 4,938,740 A | 7/1990 | Melbin |
| 4,950,238 A | 8/1990 | Sullivan |
| 4,954,126 A | 9/1990 | Wallsten |
| 4,969,896 A | 11/1990 | Shors |
| 4,994,071 A | 2/1991 | MacGregor |
| 5,005,749 A | 4/1991 | Aranyi |
| 5,007,926 A | 4/1991 | Derbyshire |
| 5,036,868 A | 8/1991 | Berggren et al. |
| 5,059,211 A | 10/1991 | Stack et al. |
| 5,061,245 A | 10/1991 | Waldvogel |
| 5,062,842 A | 11/1991 | Tiffany |
| 5,078,726 A | 1/1992 | Kreamer |
| 5,078,735 A | 1/1992 | Mobin-Uddin |
| 5,104,025 A | 4/1992 | Main et al. |
| 5,104,339 A | 4/1992 | Lazarus |
| 5,119,983 A | 6/1992 | Green et al. |
| 5,135,536 A | 8/1992 | Hillstead |
| 5,156,619 A | 10/1992 | Ehrenfeld |
| 5,178,634 A | 1/1993 | Ramos Martinez |
| 5,193,731 A | 3/1993 | Aranyi |
| 5,205,459 A | 4/1993 | Brinkerhoff et al. |
| 5,207,695 A | 5/1993 | Trout, III |
| 5,211,683 A | 5/1993 | Maginot |
| 5,234,447 A | 8/1993 | Kaster et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Ramos Martinez |
| 5,333,773 A | 8/1994 | Main et al. |
| 5,336,233 A | 8/1994 | Chen |
| 5,350,104 A | 9/1994 | Main et al. |
| 5,366,462 A | 11/1994 | Kaster et al. |
| 5,392,979 A | 2/1995 | Green et al. |
| 5,395,030 A | 3/1995 | Kuramoto et al. |
| 5,443,497 A | 8/1995 | Venbrux |
| 5,447,514 A | 9/1995 | Gerry et al. |
| 5,454,825 A | 10/1995 | Van Leeuwen |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,478,354 A | 12/1995 | Tovey et al. |
| 5,522,834 A | 6/1996 | Fonger et al. |
| 5,533,661 A | 7/1996 | Main et al. |
| 5,558,667 A | 9/1996 | Yarborough et al. |
| 5,571,167 A | 11/1996 | Maginot |
| 5,609,285 A | 3/1997 | Grant et al. |
| 5,632,433 A | 5/1997 | Grant et al. |
| 5,643,340 A | 7/1997 | Nunokawa |
| 5,669,918 A | 9/1997 | Balazs et al. |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,709,693 A | 1/1998 | Taylor |
| 5,799,857 A | 9/1998 | Robertson et al. |
| 5,817,113 A | 10/1998 | Gifford, III et al. |
| 5,833,698 A | 11/1998 | Hinchliffe et al. |
| 5,865,730 A | 2/1999 | Fox et al. |
| 5,868,763 A * | 2/1999 | Spence et al. ............... 606/153 |
| 5,879,371 A | 3/1999 | Gardiner et al. |
| 5,881,943 A | 3/1999 | Heck |
| 5,915,616 A | 6/1999 | Viola et al. |
| 5,921,995 A | 7/1999 | Kleshinski |
| 5,944,730 A | 8/1999 | Nobles et al. |
| 5,993,464 A | 11/1999 | Knodel |
| 6,015,416 A | 1/2000 | Stefanchik et al. |
| 6,024,748 A | 2/2000 | Manzo et al. |
| 6,036,700 A | 3/2000 | Stefanchik et al. |
| 6,050,472 A | 4/2000 | Shibata |
| 6,053,390 A | 4/2000 | Green et al. |
| 6,066,144 A | 5/2000 | Wolf et al. |
| 6,066,148 A | 5/2000 | Rygaard |
| 6,071,289 A | 6/2000 | Stefanchik et al. |
| 6,083,234 A | 7/2000 | Nicholas et al. |
| 6,099,553 A | 8/2000 | Hart et al. |
| 6,117,148 A | 9/2000 | Ravo et al. |
| 6,176,413 B1 | 1/2001 | Heck et al. |
| 6,179,849 B1 | 1/2001 | Yencho et al. |
| 6,187,019 B1 | 2/2001 | Stefanchik et al. |
| 6,193,129 B1 | 2/2001 | Bittner et al. |
| 6,193,734 B1 | 2/2001 | Bolduc et al. |
| 6,248,117 B1 | 6/2001 | Blatter |
| 6,251,116 B1 * | 6/2001 | Shennib et al. ............. 606/155 |
| 6,530,932 B1 * | 3/2003 | Swayze et al. ............. 606/144 |

FOREIGN PATENT DOCUMENTS

| | | |
|---|---|---|
| EP | 0 885 595 | 12/1998 |
| EP | 0 938 870 | 9/1999 |
| EP | 0 820 724 | 1/2000 |
| EP | 0 820 725 | 1/2000 |
| EP | 0 990 420 | 12/2000 |
| FR | 2316910 | 7/1976 |
| WO | 98/00605 | 1/1998 |
| WO | 98/19625 | 5/1998 |
| WO | 99/11178 | 3/1999 |
| WO | 99/21491 | 5/1999 |
| WO | 00/12013 | 3/2000 |
| WO | 00/59380 | 10/2000 |

* cited by examiner

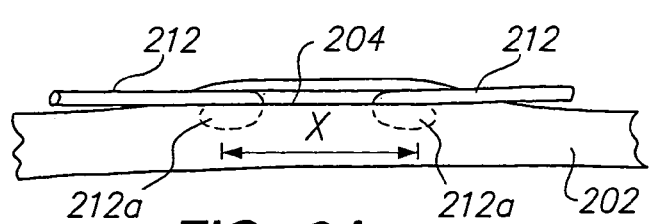
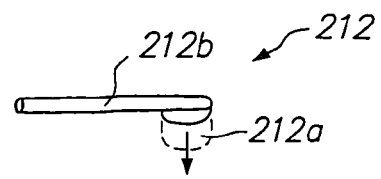
FIG. 6A  FIG. 6B
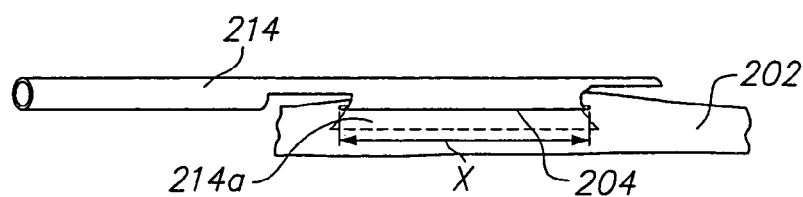
FIG. 7A
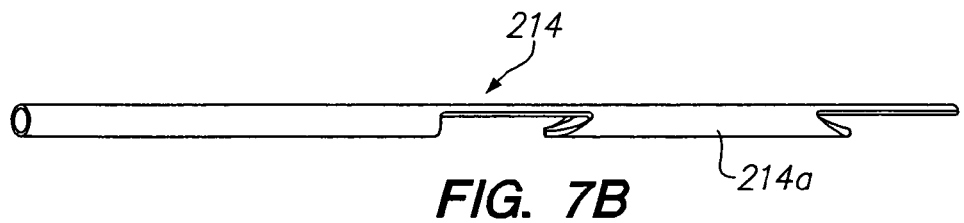
FIG. 7B
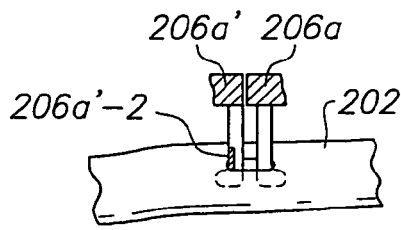
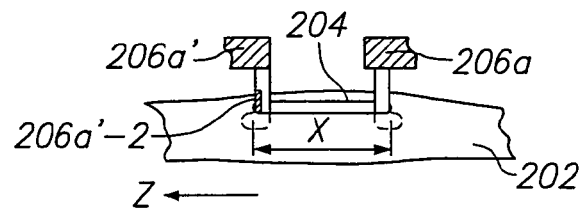
FIG. 8  FIG. 9
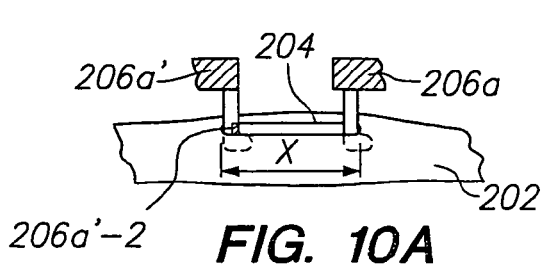
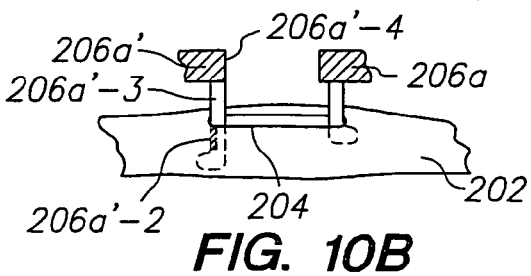
FIG. 10A  FIG. 10B

METHOD FOR TENSIONING AN INCISION DURING AN ANASTOMOSIS PROCEDURE

This application is a continuation of U.S. patent application Ser. No. 09/764,218, filed on Jan. 16, 2001, now abandoned which is incorporated by reference in its entirety.

BACKGROUND OF THE INVENTION

1. Field of the Invention

The present invention relates generally to preparing blood vessels for a vascular anastomosis procedure and more particularly to a system and method for forming and holding precise incisions in a target vessel.

2. Description of Related Art

Vascular anastomosis is a procedure where two separate blood vessels of a patient are surgically grafted together. The vascular anastomosis procedure is routinely performed during the treatment of a variety of conditions, including coronary artery disease, diseases of the great and peripheral vessels, organ transplantation and other types of trauma. When a patient suffers from coronary artery disease (CAD), an occlusion or stenosis in a coronary artery restricts blood flow to the heart muscle. In order to treat CAD, the area where the occlusion occurs is bypassed. The area is bypassed through rerouting blood flow by grafting a vessel in the form of either a prosthesis, a harvested artery or a vein. When the vessel is grafted to bypass the blocked coronary artery, the occlusion is avoided and adequate blood flow is restored to the heart muscle. This treatment is known as coronary artery bypass grafting (CABG).

When a CABG is performed, a large incision is made in the chest of a patient and the sternum is separated in order to allow access to the heart of the patient. Moreover, the patient is connected to a heart lung machine which circulates the blood of the patient. After the heart lung machine is connected to the patient, the patient's heart is stopped in order to perform the vascular anastomosis. However, stopping the patient's heart is very traumatic to the patient.

In order to minimize the trauma to the patient induced by the CABG, less invasive techniques have been used. These less invasive techniques include performing a series of small incisions in the patient's chest. Once the incisions are completed, surgery is performed with the aid of visualizing scopes. The less invasive techniques may be performed on a beating heart in order minimize trauma to the patient, thereby avoiding the need for cardiopulmonary bypass.

In both the conventional and less invasive CABG techniques, a surgeon makes an incision in a coronary artery in order to allow grafting of a graft vessel to the coronary artery. However, as the surgeon makes an incision in the coronary artery, an incision without a definable geometry results, as shown with respect to FIG. 1. FIG. 1 is a schematic of a top view of a coronary artery 102 after the formation of an incision by a surgeon in accordance with the prior art. During both the conventional and less invasive CABG techniques, a surgeon forms an incision 104 in the coronary artery 102 as shown with respect to FIG. 1. As those skilled in the art will appreciate, the incision 104 includes walls 104a and 104b which do not define a geometry. The imprecise geometry of the incision 104, as illustrated by the walls 104a and 104b, make grafting a graft vessel to the coronary artery 102 difficult.

In addition, as may be seen with respect to FIG. 1, the incision 104 is not held in place. Instead, the geometry of the incision 104 is dictated by the orientation of the coronary artery 102. To further illustrate, if the coronary artery 102 shifts during an anastomotic procedure, the geometry of the incision 104 changes, thereby making grafting even more difficult. As a result, suturing a graft vessel to the coronary artery requires a greater amount of time and surgical skill, thereby increasing the overall cost to perform an anastomotic procedure.

Furthermore, once the surgeon makes the incision 104 in the coronary artery 102, the surgeon must suture a graft vessel to the coronary artery 102. Typically, the surgeon sutures the graft vessel to the coronary artery by hand sewing the vessel using a needle the size of an eyelash. As may be appreciated, this technique requires a great amount of skill on the part of the surgeon and a great amount of time. Thus, both the time and financial costs are greatly increased for the patient. In addition, during both the conventional techniques and the less-invasive techniques, the possibility of trauma to the patient is further increased due to the greater amount of time required to perform the surgery.

In addition to suturing, other methods used during an anastomosis to graft a graft vessel to a coronary artery involves the use of an automated anastomosis instrument. However, when an automated anastomosis instrument is used, accurate location of the tissue is important to achieve accurate and leak-proof grafting.

Accordingly, a need exists for a method to form and hold incisions having a definable geometry in order to allow precise grafting of a graft vessel to a target vessel. This new method should minimize the time associated with grafting a graft vessel to a target vessel, thereby decreasing the possibility of trauma to a patient resulting from a long anastomotic procedure. Also, the new method should minimize the time associated with grafting a graft vessel to a target vessel by providing both a method allowing precise incisions in a target vessel and a simplified method for attaching the graft vessel to the target vessel once the incision is made.

BRIEF SUMMARY OF THE INVENTION

The present invention fills the aforementioned needs by providing a method for tensioning incisions in a target vessel. The present invention also provides a system for tensioning incisions in a target vessel such that the incisions have a known geometry with a predetermined length.

In one embodiment of the present invention, a method for grafting a graft vessel to a target vessel during an anastomosis procedure is disclosed. The method comprises forming an incision in the target vessel and placing incision tensioners within the incision. Upon placement of the incision tensioners within the incision, the incision tensioners tension the target vessel by pulling the incision taut. Once the incision is tensioned, the graft vessel is grafted to the target vessel using any suitable technique, including welding, clips, staples, or the like.

In a further embodiment of the present invention, a method for forming an incision in a target vessel for an anastomosis procedure is disclosed. The method comprises inserting a first incision tensioner and a second incision tensioner through a wall of the target vessel. After the incision tensioners are inserted in the wall of the target vessel, the first incision tensioner is separated from the second incision tensioner. When the first incision tensioner is separated from the second incision tensioner, the incision is tensioned to a predetermined length having a known geometry.

In another embodiment of the present invention, a system for grafting a graft vessel to a target vessel having an incision formed therein is disclosed. The system comprises first and second incision tensioners, a tensioning device body and a tensioning mechanism. The first and second incision tensioners are configured for placement within the incision of the target vessel. In addition, the incision tensioners are configured to tension the incision to a predetermined length having a known geometry once the incision tensioners are placed within the incision of the target vessel. The tensioning device body connects to both the first incision tensioner and the second incision tensioner with the tensioning mechanism. The tensioning mechanism moves the first incision tensioner with respect to the second incision tensioner in order to tension the incision in the target vessel.

As may be appreciated, the present invention provides a method for tensioning incisions to a predetermined length in a target vessel. In addition, the present invention provides a method for maintaining a known geometry of the incision during an anastomosis procedure. Therefore, the prior art problems associated with the an incision having a non-definable geometry are avoided. Furthermore, the predetermined length and the known geometry of the incisions allow for precise grafting of a graft vessel to the target vessel in a time efficient and cost efficient manner.

BRIEF DESCRIPTION OF THE SEVERAL VIEWS OF THE DRAWINGS

Many advantages of the present invention will be apparent to those skilled in the art with a reading of this specification in conjunction with the attached drawings, wherein like reference numerals are applied to like elements and wherein:

FIG. 6A is a schematic perspective view of an incision where balloons are used to hold the incision, in accordance with one embodiment of the present invention.

FIG. 6B is a side view of a balloon assembly shown with reference to FIG. 6A, in accordance with one embodiment of the present invention.

FIG. 7A is a schematic perspective view of an embodiment of the present invention where an anvil is used to hold an incision.

FIG. 7B is a perspective view of the anvil shown with respect to FIG. 7A.

FIG. 8 is a schematic perspective view of the target vessel shown with reference to FIG. 5A, where a hook includes a cutting surface, in accordance with one embodiment of the present invention.

FIG. 9 is a schematic perspective view of the target vessel shown with reference to FIG. 8, where the incision has been formed in the target vessel with the hook, in accordance with one embodiment of the present invention.

FIG. 10A is a schematic perspective view of the target vessel shown with respect to FIG. 9, where a cutting surface rotates away from the target vessel, in accordance with one embodiment of the present invention.

FIG. 10B is a schematic perspective view of the target vessel shown with reference to FIG. 9, where a cutting surface is lowered within the target vessel in order to prevent additional lengthening of the target vessel, in accordance with one embodiment of the present invention.

DETAILED DESCRIPTION OF THE INVENTION

A method for tensioning an incision on a target vessel during an anastomosis procedure is disclosed. The incision is tensioned in a target vessel in order to facilitate grafting of a vessel to the target vessel during the anastomosis procedure. Furthermore, the tensioned incision allows for proper aligning of a graft vessel with a target vessel. As used herein, an incision is tensioned when the incision is pulled taut. In accordance with another embodiment of the present invention, the incision may also be tensioned by stretching the incision with incision tensioners. The incision is pulled taut when the edges of the incision are substantially straight and parallel to one another, as will be described in much greater detail with respect to accompanying Figures. In addition, as will be further described with reference to the accompanying Figures, the incision tensioners may be any device suitable for pulling an incision taut, such as hooks, pins or the like.

Figure 2:
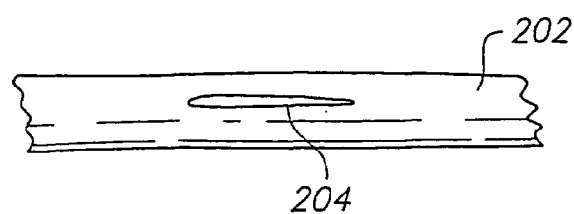
FIG. 2 is a top view of a target vessel after the formation of an incision, in accordance with one embodiment of the present invention.

Now making reference to the Figures, and more particularly to FIG. 2, FIG. 2 is a top view of the target vessel 202 after the formation of the incision 204. The incision 204 is formed in order to allow the grafting of a graft vessel (shown in FIG. 13) to the target vessel 202 at the point of the incision 204 in an end to side anastomosis. The incision 204 is formed using any suitable technique, such as punching a hole, or slicing with a scalpel, knife, shears or the like. Once the incision 204 is formed, the incision 204 is pulled taut as shown with reference to FIG. 3A.

Figure 3A:
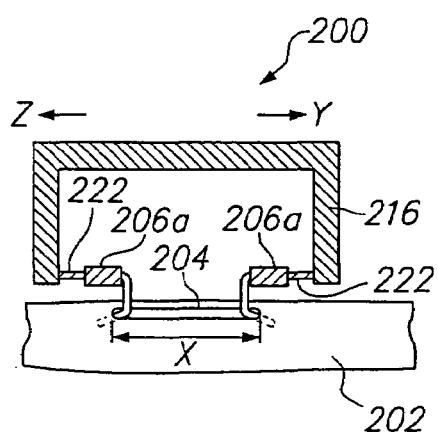
FIG. 3A is a schematic perspective view of the target vessel shown with reference to FIG. 2, where the incision is pulled taut with hooks, in accordance with one embodiment of the present invention.

FIG. 3A is a schematic showing a perspective view of the target vessel 202 shown with reference to FIG. 2, where the incision 204 is tensioned with an incision tensioning system 200. In one embodiment of the present invention, the incision tensioning system 200 aligns a graft vessel (shown with reference to FIG. 13) with the target vessel 202. The incision tensioning system 200 includes tensioners 222, a bracket 216 and hooks 206a. The tensioners 222 provide a force to the hooks 206a such that the hooks 206a tension the incision 204. In accordance with one embodiment of the present invention, the tensioners 222 may be any device suitable for providing a tensioning force on the hooks 206A such as a spring, a threaded fastener, or the like. The bracket 216 provides structural support for the tensioners 222 and the hooks 206a such that the tensioners 222 provide a tensioning force to the hooks 206a in order to tension the incision 204.

Figure 1:
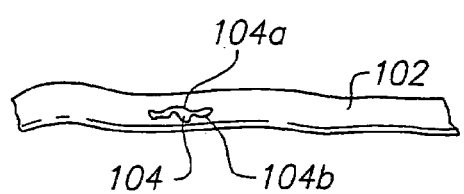
FIG. 1 is a schematic top view of a coronary artery after incision by a surgeon in accordance with the prior art.

The hooks 206a are inserted into ends of the incision 204, as shown with reference to the Figure. The hooks 206a are configured to engage the ends of the incision 204 such that the hooks 206a pull the incision 204 taut to form a known geometry in which the sides of the incision 204 are substantially straight and parallel, as shown with respect to FIG. 3A. In accordance with one embodiment of the present invention, the known geometry is defined as the ability of the geometry of the incision 204 to remain constant during an anastomosis procedure. As described with reference to the prior art of FIG. 1, the prior art incisions formed in a target vessel were not pulled taut and did not have a known geometry. Therefore, the geometry of the prior art incision changes as a surgeon performs an anastomosis procedure, as opposed to the present invention.

In accordance with an embodiment of the present invention, the incision 204 is taut when the incision 204 is tensioned to a predetermined length X. The predetermined length X of the incision 204 corresponds to a width of a compressed graft vessel (shown with reference to FIG. 13) to be grafted to the target vessel 202 during the anastomosis procedure. When the incision 204 is tensioned to the predetermined length X, proper grafting of the graft vessel to the target vessel 202 is ensured. In one embodiment of the present invention, the incision 204 is tensioned by preferably stretching in a range between about 2% of the length of the incision 204 to about 25. % of the length of the incision 204. For example, if the incision 204 has a predetermined length of 0.200 inches, the incision 204 is tensioned when the hooks 206a stretch the incision to a predetermined length of 0.220 inches. Additionally, in accordance with another embodiment of the present invention, the hooks 206a may be pulled with a predetermined force as denoted by directional arrows Y and Z. In one embodiment of the present invention, the predetermined tensioning force is in a range preferably of about 0.001 N to about 4.5 N and more preferably about 0.65 N. Incision tensioning is provided by pulling on the hooks 206a until the incision 204 is tensioned to the predetermined length X. The incision may be measured using any suitable technique to ascertain the proper length.

Figure 3B:
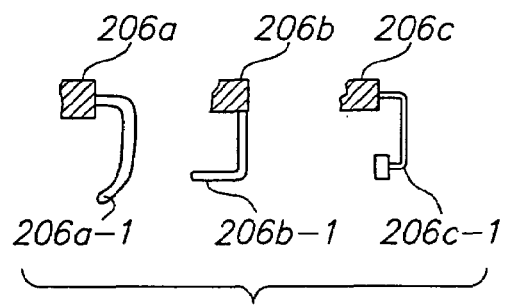
FIG. 3B is a side view of alternative embodiments of the hooks as shown with reference to FIG. 3A, in accordance with one embodiment of the present invention.

It should be noted that the hooks 206a may have any configuration suitable for engaging ends of the incision 204, as shown with reference to FIG. 3B. FIG. 3B is a side view of alternative embodiments of the hooks 206a as shown with reference to FIG. 3A, in accordance with one embodiment of the present invention. Hooks 206a, 206b and 206c include ends 206a-1, 206b-1 and 206c-1. The ends 206a-1, 206b-1 and 206c-1 are configured to engage the incision 204 once the hooks 206a, 206b and 206c are inserted in the incision 204, as shown with reference to FIG. 3A. Therefore, after the hooks 206a, 206b and 206c are inserted in the incision 204, the ends 206a-1, 206b-1 and 206c-1 engage tissue to pull the incision 204 taut. In addition to the hooks 206a, 206b and 206c, pins 208a may also be used to pull the incision 204 taut, as shown with reference to FIG. 4A.

Figure 4A:
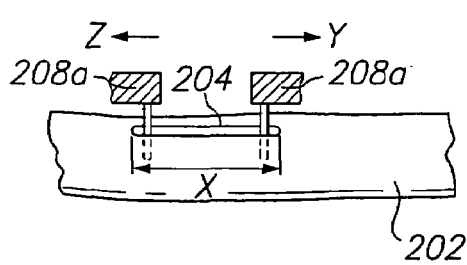
FIG. 4A is a schematic perspective view of an embodiment of the present invention where pins pull the incision shown with reference to FIG. 3A taut.

FIG. 4A is a side view of the incision 204 shown with reference to FIG. 3A, where the pins 208a are inserted in the incision 204 to tension the incision 204, in accordance with one embodiment of the present invention. As described with reference to FIG. 3A, the pins 208a tension the incision 204 by pulling the incision 204 taut using the tensioners 222 until the incision 204 is tensioned to the predetermined length X. Alternatively, the pins 208a may be pulled with a predetermined force along the directional arrows Y and Z, as described with reference to FIG. 3A. In addition to the pins 208a, any pin having a configuration suitable for pulling the incision 204 taut may be used to stretch the incision 204 to the predetermined length X, as shown with respect to FIG. 4B.

Figure 4B:
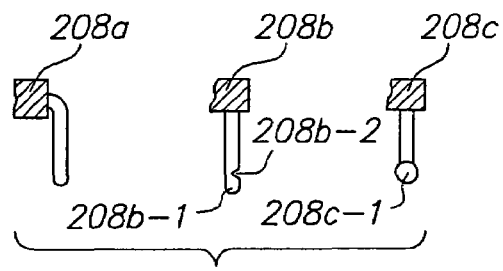
FIG. 4B is a side view of alternative embodiments of pins which may be used to hold the incision shown with respect to FIG. 4A, in accordance with one embodiment of the present invention.

FIG. 4B shows pins 208a, 208b and 208c which may be used to tension the incision 204 to the predetermined length X, in accordance with one embodiment of the present invention. The pins 208b and 208c include ends 208b-1 and 208c-1. The end 208b-1 includes a groove 208b-2 which is configured to engage the incision 204 as the pin 208b is inserted into the incision 204. The end 208c-1 is configured to engage the incision 204 as the pin 208c is inserted into the incision 204. In addition to the pins 208a through 208c, sutures 210a may be used to tension the incision 204 to the predetermined length X, as shown with reference to FIGS. 5A and 5B.

Figure 5A:
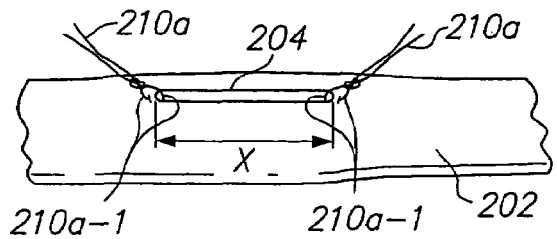
FIG. 5A illustrates a schematic perspective view of an embodiment of the present invention where sutures are used to hold the incision shown with respect to FIG. 4A to a critical dimension.

FIG. 5A illustrates a side view of the incision 204 shown with respect to FIG. 4A, where the sutures 210a tension the incision 204 to the predetermined length X. In this embodiment, the sutures 210a include ends 210a-1 which are attached to the ends of the incision 204 and knotted in a conventional manner as shown with respect to FIG. 5A. Once the sutures 210a are formed, the sutures 210a pull the incision 204 taut in order to tension the incision 204. In addition to the knotted sutures 210a, unknotted sutures 210b, as shown with respect to FIG. 5B, may also be used to tension the incision 204 to the predetermined length X.

Figure 5B:
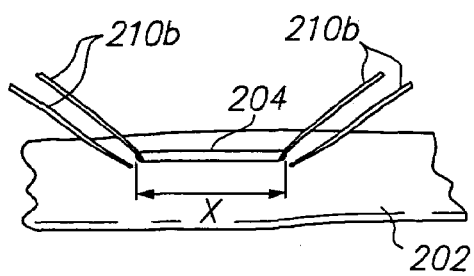
FIG. 5B is a schematic perspective view of an embodiment of the present where sutures are used to hold an incision.

FIG. 5B illustrates a side view of the incision 204 shown with respect to FIG. 4A, where the sutures 210b are used to tension the incision 204 to the predetermined length X. In this embodiment, the sutures 210b are formed such that the sutures 210b stet through ends of the incision 204, as shown with reference to FIG. 5B. Once the sutures 210b are secured to the ends of the incision 204, the sutures are pulled taut to tension the incision 204 to the predetermined length X. In addition to the sutures 210a and 210b, a balloon assembly 212 may be used to tension the incision 204 to the predetermined length X, as shown with respect to FIG. 6A.

FIG. 6A shows a side view of the incision 204 shown with reference to FIG. 5B, where the balloon assembly 212 tensions the incision 204 to the predetermined length X. The balloon assembly 212 includes a balloon 212*a* rigidly coupled with a member 212*b*, as shown with reference to FIG. 6B. When the balloons assemblies 212 are inserted into the incision 204, the balloons 212*a* are in an uninflated configuration in order to facilitate placement within the incision 204. Once the balloons 212*a* are placed within the incision 204, the balloons 212*a* are inflated using any suitable technique. Upon inflation, the balloon assemblies 212 are used to tension the incision 204. The balloon assemblies 212 tension the incision 204 by pulling the balloon assemblies 212 taut within the incision 204 to tension the incision 204 into the predetermined length X, as shown with respect to FIG. 6A. It should also be noted that the balloon assemblies 212 may tension the incision 204 to the predetermined length X with the predetermined force, as previously described.

In addition to the balloons 212*a*, a member 214 may also be used to tension the incision 204 to the predetermined length X, as shown with reference to FIG. 7A. Once the incision 204 is made, the member 214 is placed within the incision 204 in order to tension the incision to the predetermined length X, as shown with respect to FIG. 7A. The member 214 includes an anvil 214*a* (shown with reference to FIG. 7B) which is configured for insertion in the incision 204 in order to tension the incision 204 to the predetermined length X. Thus, upon placement of the member 214 within the incision 204, the anvil 214*a* tensions the incision 204 to the predetermined length X.

As previously stated, the incision 204 is formed using any suitable technique, such as slicing with a scalpel, knife, shears or the like. Nonetheless, in accordance with another embodiment of the present invention, the incision 204 may be tensioned by a hook 206*a*' configured to include a cutting surface 206*a*'-2, as shown with reference to FIG. 8. FIG. 8 is a side view of the target vessel. 202 shown with reference to FIG. 5A, where the hook 206*a*' includes the cutting surface 206*a*'-2, in accordance with one embodiment of the present invention. The cutting surface 206*a*'-2 is configured to form an incision in the target vessel 202 in order to allow tensioning of the incision 204 to the predetermined length X. In one embodiment of the present invention, the cutting surface 206*a*'-2 may be any sharpened surface suitable for forming an incision in the target vessel 202, including a blade or the like. Once the hooks 206*a* and 206*a*' are inserted into the target vessel 202, the hook 206*a*' moves away from the hook 206*a* to form the incision 204, as shown with reference to FIG. 9.

FIG. 9 illustrates a side view of the target vessel 202 shown with reference to FIG. 8, illustrating the formation of the incision 204 in the target vessel 202 with the hook 206*a*', in accordance with one embodiment of the present invention. The cutting surface 206*a*'-2 forms the incision 204 as the hook 206*a*' moves in a direction denoted by the directional arrow Z. After the incision 204 is formed, the cutting surface 206*a*'-2 is removed from an edge of the incision 204, as shown with reference to FIG. 10A.

FIG. 10A illustrates a side view of the target vessel 202 shown with respect to FIG. 9, where the cutting surface 206*a*'-2 rotates away from the edge of the incision 204 in order to prevent further cutting of the incision 204, in accordance with one embodiment of the present invention. In this embodiment, the cutting surface 206*a*'-2 rotatably attaches to the hook 206*a*' using any suitable technique, including pins, a bearing assembly, or the like. After the cutting surface 206*a*'-2 rotates away from the edge of the incision 204, the hooks 206*a* and 206*a*' tension the incision 204 to the predetermined length X. In addition to rotating the cutting surface 206*a*'-2 away from the edge of the incision 204, as shown with reference to FIG. 10A, the cutting surface 206*a*'-2 may be lowered within the target vessel 202 such that the cutting surface 206*a*'-2 does not contact the edge of the incision 204, as shown with respect to FIG. 10B.

FIG. 10B is a side view of the target vessel 202 shown with reference to FIG. 10A, where the cutting surface 206*a*'-2 lowers within the target vessel 202 upon formation of the incision 204, in order to prevent additional cutting of the target vessel 202, in accordance with one embodiment of the present invention. In this embodiment, the configuration of the hook 206*a*' allows lowering of the cutting surface 206*a*'-2 using any suitable technique, including a piston-type assembly where the hook 206*a*' includes a pin 206*a*'-3 having the cutting surface 206*a*'-2. In this embodiment, the pin 206*a*'-3 is configured to slide into and out of a base 206*a*'-4 of the hook 206*a*'. Thus, upon formation of the incision 204, the piston 206*a*'-3 lowers the cutting surface 206*a*'-2 within the target vessel 202. Upon lowering the cutting surface 206*a*'-2, the hooks 206*a* and 206*a*' tension the incision 204 to the predetermined length X.

Figure 11:
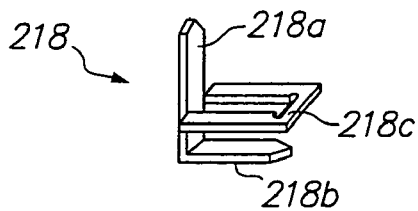
FIG. 11 is a perspective view of an incision tensioning clip capturing a graft vessel and a target vessel, in accordance with one embodiment of the present invention.

In addition to the hooks 206*a* and 206*a*', the incision 204 may also be tensioned using an incision tensioning clip 218, as shown with reference to FIG. 11. The incision tensioning clip 218 includes tines 218*a* and 218*b* and a body 218*c*. The tines 218*a* and 218*b* are configured to penetrate vessels and rotate or fold over toward the body 218*c* upon vessel penetration in order to capture a vessel, as shown with reference to FIGS. 12 and 13.

Figure 12:
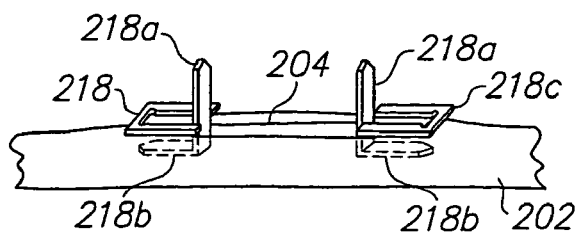
FIG. 12 is a perspective view of the target vessel shown with respect to FIG. 10B, where incision tensioning clips have been inserted into the target vessel, in accordance with one embodiment of the present invention.

FIG. 12 is a perspective view of the target vessel 202 shown with respect to FIG. 10B, where the incision tensioning clips 218 have been inserted into the target vessel 202, in accordance with one embodiment of the present invention. The incision tensioning clips 218 tension the incision 204 to the predetermined length X and capture a graft vessel 220 (shown in FIG. 13) with the target vessel 202. After the incision 204 is formed, the tine 218*b* of the incision tensioning clip 218 is inserted within the target vessel 202 such that the incision tensioning clip 218 traps a target vessel wall of the target vessel 202 between the tine 218*b* and the body 218*c*, as shown with reference to the Figure. Once the incision tensioning clips 218 are placed within the target vessel 202, the incision 204 is tensioned and the graft vessel 220 is grafted to the target vessel 202, as illustrated with reference to FIG. 13.

Figure 13:
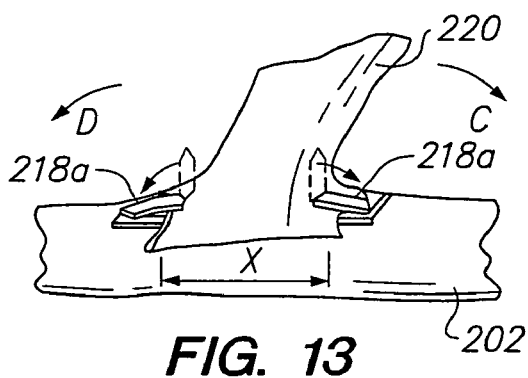
FIG. 13 is a perspective view of an embodiment of the present invention illustrating the target vessel shown with reference to FIG. 12, where a vessel is grafted to the target vessel during an anastomosis procedure using the incision tensioning clips.

FIG. 13 is a perspective view of the target vessel 202 shown with reference to FIG. 12, where the graft vessel 220 is grafted to the target vessel 202 during an anastomosis procedure. The graft vessel 220 is grafted to the target vessel 202 at the incision 204 using the incision tensioning clips 218. The tines 218*a* of the incision tensioning clips 218 penetrate the graft vessel 220 in order to secure the graft vessel 220 to the target vessel 202. Once the tines 218*a* penetrate the graft vessel 220, the tines 218*a* rotate or fold over, as indicated by directional arrows "C" and "D", in order to secure the graft vessel 220 to the target vessel 202.

Figure 14A:
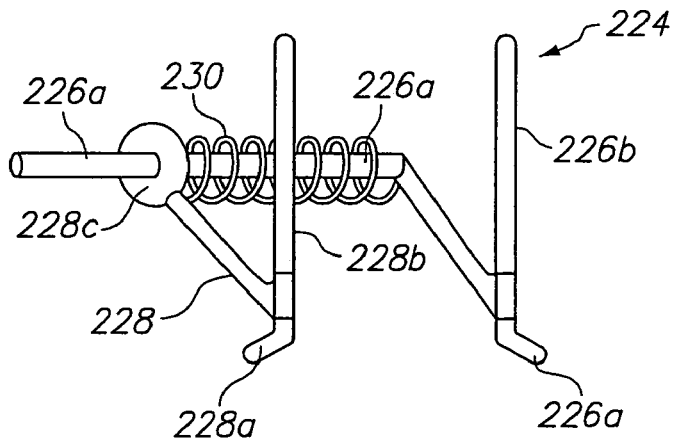
FIG. 14A is a perspective view illustrating a force controlled tension device, in accordance with one embodiment of the present invention.

As previously mentioned with reference to FIG. 3A, a predetermined force may form the incision 204 to the predetermined length X. In accordance with one embodiment of the present invention, a force controlled tension device 224, as shown with respect to FIG. 14A, applies a predetermined force to the target vessel 202 in order to form the incision 204 to the predetermined length X. The force controller tension device 224 includes tensioners 226 and 228. The tensioners 226 and 228 are configured to engage the target vessel 202 with hooks 226a and 228a, as shown with reference to FIG. 14A. It should be noted that the tensioners 226 and 228 may also be pins, or any other device suitable for engaging the target vessel 202, as described earlier. Additionally, the tensioners 226 and 228 include removable sections 226b and 228b which allow for precise placement of the graft vessel 220 to the target vessel 202. The removable sections 226b and 228b are removed once the graft vessel 220 is placed over the removable sections 226b and 228b and the graft vessel 220 is brought into contact with tensioners 226 and 228, as will be discussed more fully with respect to FIGS. 15A and 15B.

In accordance with one embodiment of the present invention, the tensioner 228 engages with the tensioner 226 via a notch 228c. The notch 228c is configured such that the tensioner 228 slidably attaches to the tensioner 226, as shown in the Figure. The force controller tension device 224 also includes a spring 230 which imparts a force on the tensioner 228 in order to separate the tensioner 228 from the tensioner 226 upon insertion of the force controller tension device 224 within the target vessel 202, as shown with reference to FIG. 15A. The spring 230 may be any spring suitable for separating the tensioner 228 from the tensioner 226, such as a compression spring or the like. In accordance with one embodiment of the present invention, the spring 230 imparts a force preferably in a range of about 0.001 N to about 4.5 N and more preferably about 0.65 N. It should be noted that alternative techniques may be used to separate the tensioner 228 from the tensioner 226 in addition to the spring 230 using any suitable force applying mechanism, such as a torque applying DC motor or the like.

Figure 14B:
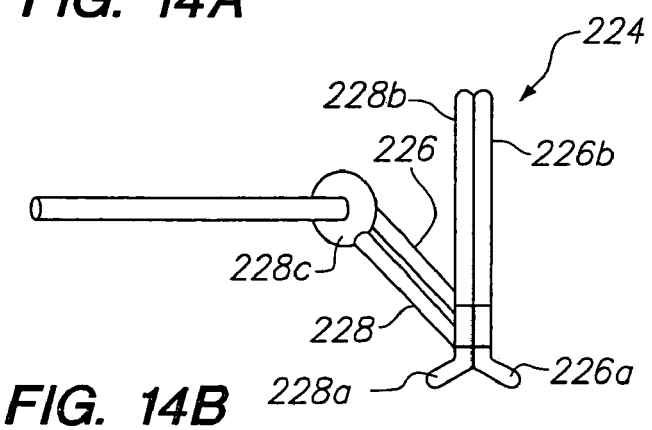
FIG. 14B illustrates a perspective view of the force controlled tension device shown with reference to FIG. 14A, where the force controlled tension device is configured for insertion into a target vessel.
Figure 15A:
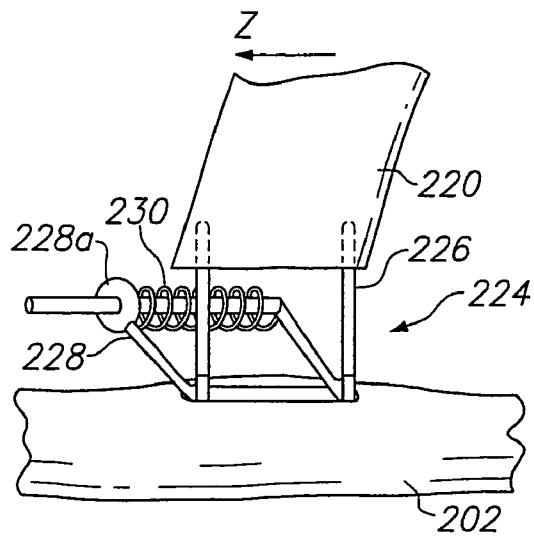
FIG. 15A is a schematic perspective view of the force controlled tension device shown with respect to FIG. 14A forming an incision in a target vessel, in accordance with one embodiment of the present invention.
Figure 15B:
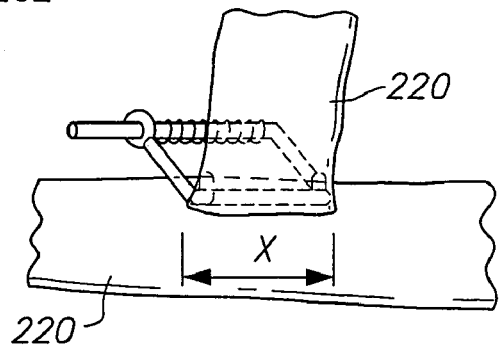
FIG. 15B is an embodiment of the present invention showing the force controlled tension device shown with reference to FIG. 15A, where the force controlled tension device forms an incision in a target vessel to a predetermined length X.

Turning to FIG. 15A, FIG. 15A illustrates the insertion of the force controller tension device 224 within the target vessel 202, in accordance with one embodiment of the present invention. Prior to insertion within the target vessel 202, the tensioners 226 and 228 are adjacent to one another to form a single unit as shown with reference to FIG. 14B. Upon insertion of the force controller tension device 224 within the target vessel 202, the spring 230 moves the tensioner 228 in the direction Z in order to form the incision 204 to the predetermined length X, as shown with reference to FIG. 15B. In one embodiment of the present invention, once the force controller tension device 224 forms the incision 204 to the predetermined length X, the graft vessel 220 is placed over the removable sections 226b and 228b. The removable sections 226b and 228b are then removed in order to allow grafting of the graft vessel 220 to the target vessel 202 as shown with reference to FIG. 15B.

Figure 16:
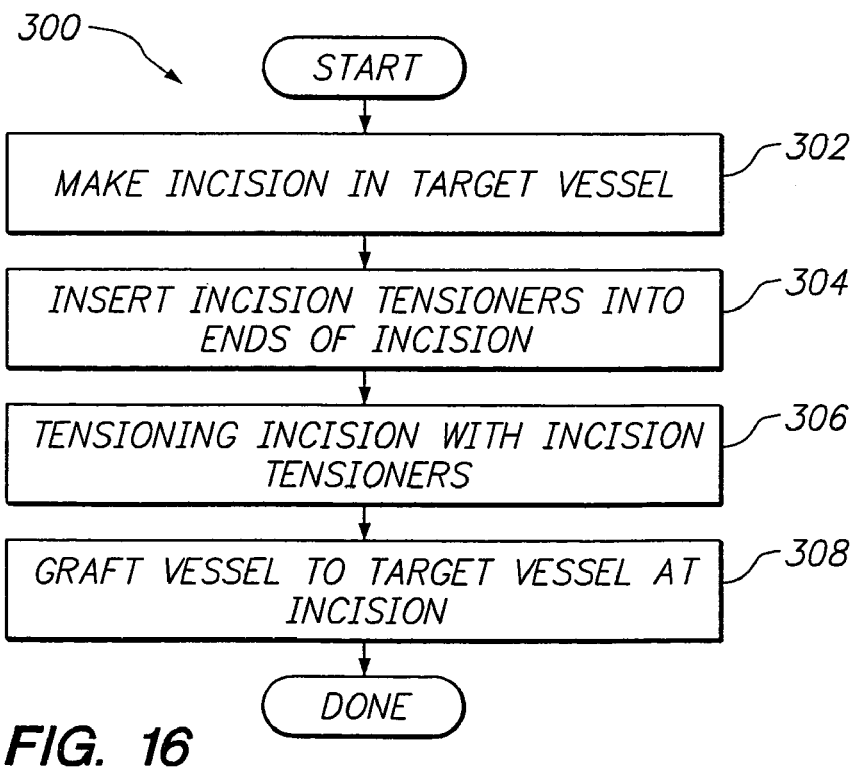
FIG. 16 is a flow chart illustrating a method for incision tensioning a target vessel, in accordance with one embodiment of the present invention.

Now making reference to FIG. 16, FIG. 16 illustrates a method 300 for tensioning an incision in a target vessel, in accordance with one embodiment of the present invention. In an operation 302, an incision is made in a target vessel. The incision allows for grafting of a graft vessel to the target vessel during an end to side anastomosis procedure. Once the incision is made in the target vessel, incision tensioners are inserted into ends of the incision in an operation 304. The incision tensioners may include any structure suitable for providing tension to an incision, including the previously described anvil, hooks, pins, balloons and clips. For example, making reference to FIG. 3A, an incision 204 is made in the target vessel 202 in the operation 302. Once the incision is made, hooks 206a are inserted into the incision. After insertion of the hooks 206a, an operation 306 is performed.

In the operation 306, the incision tensioners pull the incision taut. In one embodiment of the present invention, the incision tensioners are considered taut when the incision is tensioned to a predetermined length. It should also be noted that when the incision tensioners are pulled taut, the tensioners maintain a known geometry of the incision. Turning back to the example and FIG. 3A, the hooks 206a are pulled taut until the incision 204 is tensioned to the predetermined length X. As previously stated, the predetermined length X allows for proper grafting of a graft vessel to the target vessel during an anastomosis procedure by matching the incision length to a graft vessel size. Turning back to the method 300, once the incision tensioners pull the incision taut, a graft vessel is grafted to the target vessel at the incision site during an anastomosis procedure in an operation 308. The performed anastomosis procedure which connects the graft vessel to the target vessel may include suturing, stapling, clipping and deploying an automatic anastomosis device. Furthermore, the performed anastomosis procedure may include RF tissue welding, laser tissue welding, adhesive application, or other connecting methods.

Referring back to the example and FIG. 13, in one embodiment, the graft vessel 220 is secured to the target vessel 202 using the incision tensioning clip 218, as shown with reference to FIG. 13. As described earlier, the incision tensioning clip 218 includes the tines 218a and 218b which engage both the graft vessel 220 and the target vessel 202. Also as described earlier, the tines 218a and 218b are configured to rotate once the tines 218a and 218b penetrate the vessels 202 and 220 in order to capture the target vessel 202 and the graft vessel 220, as shown with respect to FIG. 13. Additional securing mechanisms, such as staples, clips or tissue welding may be used to secure the edges of the incision to the graft vessel to complete the anastomosis procedure. After the operation 308 is performed, the method 300 is complete.

As may be appreciated, the present invention provides a precise method for aligning a graft vessel to a target vessel in a time efficient and cost efficient manner. The incision tensioners maintain a known geometry for an incision during an anastomosis procedure. Therefore, a surgeon may precisely graft a graft vessel to a target vessel containing the incision. The present invention is preferably used with a stapling anastomosis device or anastomosis clips, such as incision tensioning clips, which obviate the need for suturing during an anastomosis procedure. Therefore, both the amount of time required to graft vessels and the attendant costs are greatly decreased. Moreover, the present invention greatly reduces the possibility of trauma to the patient due to the reduced amount of time required to graft vessels.

The above are exemplary modes of carrying out the invention and are not intended to be limiting. It will be apparent to those of ordinary skill in the art that modifications thereto can be made without departure from the spirit and scope of the invention as set forth in the following claims.

What is claimed is:

1. A method for connecting a graft vessel to a target vessel, each vessel having a wall bounding a lumen, comprising:
   creating an incision in the wall of the target vessel;
   inserting at least two members into the incision;
   moving at least two of said members to apply tension to the incision;
   connecting the graft vessel to the target vessel during said applying; and
   removing said members from the incision after said connecting.

2. The method of claim 1, wherein said applying stretches the incision to a substantially constant length during said connecting.

3. The method of claim 2, further comprising determining said length before said creating.

4. The method of claim 2, wherein said substantially constant length corresponds to the diameter of the lumen of the graft vessel.

5. The method of claim 1, wherein said tension is in a range of about 0.001 N to about 4.5 N.

6. The method of claim 1, wherein said creating is performed substantially along a longitudinal direction relative to the target vessel.

7. The method of claim 1, wherein said moving is performed substantially along a longitudinal direction relative to the target vessel.

8. The method of claim 1, wherein said connecting is performed between an end of the graft vessel and the side of the target vessel.

9. The method of claim 1, wherein at least one said member is a pin.

10. The method of claim 1, wherein at least one said member is a hook.

11. The method of claim 1, wherein at least one member includes a cutting surface, and wherein said creating is performed at least in part with said cutting surface.

12. The method of claim 1, wherein said members are spaced-apart flanges at opposite ends of an anvil.

13. The method of claim 1, further comprising biasing at least two of said members away from one another.

14. The method of claim 13, further comprising applying a force to at least two of said members against said bias during said inserting.

15. The method of claim 13, wherein said biasing is performed by a spring.

16. The method of claim 1, wherein said connecting includes suturing the graft vessel to the target vessel.

17. The method of claim 1, wherein said connecting includes stapling the graft vessel to the target vessel.

18. The method of claim 1, wherein said creating is performed with a scalpel.

19. The method of claim 1, further comprising selecting a fixed length, wherein said moving is performed until the length of the incision is substantially equal to said fixed length.

20. The method of claim 1, wherein at least one of said members is movably connected to a bracket.

* * * * *